(12) United States Patent
Nedelman

(10) Patent No.: US 10,238,146 B2
(45) Date of Patent: Mar. 26, 2019

(54) HOOKAH VAPORIZOR MACHINE

(71) Applicant: Brandon Nedelman, oceanside, CA (US)

(72) Inventor: Brandon Nedelman, oceanside, CA (US)

(73) Assignee: brandon nedelman, oceanside, CA (US)

( * ) Notice: Subject to any disclaimer, the term of this patent is extended or adjusted under 35 U.S.C. 154(b) by 0 days.

(21) Appl. No.: 15/055,582

(22) Filed: Feb. 27, 2016

(65) Prior Publication Data
US 2017/0245548 A1    Aug. 31, 2017

Related U.S. Application Data

(63) Continuation-in-part of application No. 15/055,591, filed on Feb. 27, 2016.

(51) Int. Cl.
*A24F 1/30* (2006.01)
*A24F 47/00* (2006.01)

(52) U.S. Cl.
CPC .............. *A24F 47/008* (2013.01); *A24F 1/30* (2013.01)

(58) Field of Classification Search
CPC ................................ A24F 47/008; A24F 1/30
USPC ....................................................... 131/329
See application file for complete search history.

(56) References Cited

U.S. PATENT DOCUMENTS

| | | | | |
|---|---|---|---|---|
| 13,260 A | * | 7/1855 | Gartley et al. | ........ F04D 29/441 |
| | | | | 415/207 |
| 700,088 A | * | 5/1902 | Reschke | ................... A24F 1/30 |
| | | | | 131/173 |
| 3,050,255 A | | 8/1962 | Willson | |
| 3,765,180 A | | 10/1973 | Brown | |
| 3,994,307 A | * | 11/1976 | Loeffler | ............... A24C 5/3406 |
| | | | | 131/330 |
| 4,153,933 A | | 5/1979 | Blume, Jr. | |
| 4,265,211 A | | 5/1981 | Meloeny | |
| 4,268,906 A | | 5/1981 | Bourke | |
| 4,643,394 A | | 2/1987 | Shimura | |
| 4,942,516 A | | 7/1990 | Hyatt | |
| 4,979,878 A | * | 12/1990 | Short | ...................... F04B 53/14 |
| | | | | 417/255 |
| 6,263,908 B1 | | 7/2001 | Love | |
| 6,497,554 B2 | | 12/2002 | Yang | |
| 6,548,837 B1 | | 4/2003 | Vaz De Azevedo | |
| 6,932,101 B2 | | 8/2005 | Home | |
| 7,060,922 B2 | | 7/2006 | Hoehne | |
| 7,182,311 B2 | | 2/2007 | Kimble | |
| 7,832,410 B2 | | 11/2010 | Hon | |
| D658,539 S | | 5/2012 | Harshman | |
| 8,365,742 B2 | | 2/2013 | Hon | |
| 8,375,957 B2 | | 2/2013 | Hon | |
| 8,393,331 B2 | | 3/2013 | Hon | |
| 8,490,628 B2 | | 7/2013 | Hon | |

(Continued)

*Primary Examiner* — Eric Yaary
*Assistant Examiner* — Russell E Sparks

(57) ABSTRACT

A high powered electronic cigarette machine in which the atomizer vapor output feeds into a compression chamber via forced fan induction. The compression chamber operates via a motor driven piston and is also assisted via an electromagnet. The compressed vapor is released to the end user for inhalation via a switch operating a release valve downstream of the nozzle or mouthpiece and it's release settings are adjustable via a touchscreen control and display interface.

10 Claims, 2 Drawing Sheets

(56) References Cited

U.S. PATENT DOCUMENTS

| | | |
|---|---|---|
| 8,511,318 B2 | 8/2013 | Hon |
| 8,689,805 B2 | 4/2014 | Hon |
| 8,850,835 B2 | 10/2014 | Flanigan |
| 8,863,752 B2 | 10/2014 | Hon |
| 8,893,726 B2 | 11/2014 | Hon |
| 8,899,239 B2 | 12/2014 | Hon |
| 8,910,640 B2 | 12/2014 | Sears |
| 8,910,641 B2 | 12/2014 | Hon |
| 9,095,174 B2 | 8/2015 | Capuano |
| D739,601 S | 9/2015 | Bahbah |
| 9,320,300 B2 | 4/2016 | Hon |
| 9,326,548 B2 | 5/2016 | Hon |
| 9,326,549 B2 | 5/2016 | Hon |
| 9,326,550 B2 | 5/2016 | Hon |
| 9,326,551 B2 | 5/2016 | Hon |
| 9,339,062 B2 | 5/2016 | Hon |
| 9,364,027 B2 | 6/2016 | Hon |
| 9,370,205 B2 | 6/2016 | Hon |
| 9,456,632 B2 | 10/2016 | Hon |
| 2006/0104839 A1 | 5/2006 | Burkholder |
| 2008/0105789 A1 | 5/2008 | Smith |
| 2009/0189869 A1 | 7/2009 | Nishimura |
| 2010/0221128 A1 | 9/2010 | Mellar |
| 2012/0042884 A1* | 2/2012 | Mukaddam ............... A24F 1/30 131/173 |
| 2012/0199572 A1* | 8/2012 | Shen .................... A61M 11/041 219/438 |
| 2013/0032159 A1* | 2/2013 | Capuano .................. A24F 1/30 131/329 |
| 2013/0319437 A1 | 12/2013 | Liu |
| 2015/0282524 A1 | 10/2015 | Elhalwani |
| 2016/0044960 A1* | 2/2016 | O'Connor ............. A24F 47/008 131/200 |
| 2016/0165951 A1* | 6/2016 | Gupta ...................... A24F 1/30 131/329 |
| 2016/0206001 A1* | 7/2016 | Eng ....................... A24F 47/008 |

\* cited by examiner

HOOKAH VAPORIZOR MACHINE

BACKGROUND ART

Hookah, is a smoking style with its origins rooted in ancient middle eastern culture. A hookah machine is loaded with sweet flavored tobacco, which is filtered through water, resulting in the production of large quantity of smooth smoke. The tobacco is first loaded into a chamber, and then the chamber is sealed at the top with a metal cover. The top of the chamber is heated by burning coals, as the tobacco is slowly burned and passed through a water filter. The final filtered smoke product is inhaled through a small hose and nozzle as the flavored and filtered smoke is enjoyed. The hookah experience has become very prominent and popular social experience in generation x. Teenagers and young adults often incorporated hookah into small social events.

The electronic cigarette, or vape market is relatively new and closely related to the same subcultural makeup. An electronic cigarette is a pen style device that is filled with electronic cigarette liquid. The e-liquid is converted into a smoke-able vapor by an atomizer component, via step up transformation, or a coil, prior to being vaped. The result is a smooth, water based vapor product which is inhaled through an opening at the top of the upright pen.

SUMMARY

The invention is a hookah/shisha shaped/simulation designed electronic atomization cigarette machine wherein the atomized vapor created of the machines atomizer is compressed prior to its dispense from the machine for user inhalation comprising:

Housing/shell: 101 is the machine housing or shell that is shaped like a "vase" to produce and resemble, or simulate a hookah/shisha experience. The housing contains all internal assembled components as well as provides a hookah-like appearance in design structure;

Tank: 114 is the e-juice or refillable e-liquid reservoir or tank. The reservoir/tank stores filled liquid in the machine for its function. The reservoir/tank is refillable through a junction 115 that extends from 114 the reservoir/tank to/through the outer wall of 101 the housing. Refill e-juice can be poured into the machines reservoir tank via junction 115.

The machine possesses a means of transferring reservoir liquid to the atomizer.

Atomizer: 110 is an electronic cigarette type "atomizer" or "vaporizer. It receives computer 107 controlled source battery 102 electricity at its electronic connection portions for circuit wires, 109, to perform the function of atomizing liquid e-juice thus converting it into smoke-able/inhalation vapor for the end user upon dispense from the machine.

Vapor transfer: 117 is a junction from the 110 atomizer to the machines compression chamber 118. It contains a motor 121 driven fan 122 assembly which forcefully inducts generated/produced inhalation vapor of the 110 atomizer upon distribution of computer 107 controlled source battery 102 power supply signal to the motor 121. the machine may further contain additionally means of facilitating the transfer of atomized vapor into compression chamber 118, such as routed installed vacuum lines utilizing functions inherent inside of compression chamber 118.

Compression mechanism: 112 is the driving electric motor for the machines compression mechanism. Upon receipt of computer 107 regulated source battery 102 supply electricity, 112 the electric motor responds the compression mechanism operation further comprising:

119 a compression piston, junctioned to its respective;

113 piston connecting rod, junctioning 119 the compression piston to its respective lobe on;

111 the piston crankshaft which is junctioned to 112 the compression/piston mechanism motor so that when the 112 motor is delivered electricity as such, it spins the 111 crankshafts thus responding upward and downward cycling motion of the 113 connecting rod. The motion of the 113 connecting rod directly drives the end junctioned compression piston 119 which resides in compression chamber 119. Thus, when the motor 112 is so engaged, the ultimate motion cycling of 119 the piston inside of chamber 118 creates the function of compression. As indicated, the motor/fan assembly 121/122 drives the inflow of produced vapor at 110 the atomizer into the chamber 118 wherein it is compressed prior to or consistent with its dispense from the cigarette machine for end user inhalation.

Electromagnetic Piston Assist: Inside the chamber 118 is an aimed electromagnetic rod 123 in which a step-up transformer 124 transmits power from source computer 107 control/regulation/battery 102 so that, synchronous with the operation of the electric motor 112 which drives the piston 119, on only its upward or compression motion. This on and off switching, of the transformer signal flow, is controlled by an electronic distribution timing system comprised of the following: A crankshaft position sensor (located in an applicable area relative to the crankshaft 111 internal the housing 101) which locates the crankshafts 111 position and distributes the signal to: 107 computer unit, which consisting of the very at least memory and processing functions and parts, which receives the signal and distributes on and off power to the transformer accordingly, to power the on and off switching of power supply to the electromagnetic rod 123. It receives a step up/transformed pulse signal from the computer 107 on the upward motion of the two-stroke piston 119 cycle, which is inputted by a crankshaft position sensor 125, so that on the upward motion of the piston 119, the transformer 124 pulse engages the electromagnet pulling the piston 119.

Vapor Dispense/Release: 120 dispense valve is an electronically controlled vapor flow valve respond able by user/operator engagement of 103 touchscreen panel which is fastened/assembled to be accessible at its mounting point manifesting accessibility of the touchscreen control interface on the outer housing 101 of the machine. 103 the touchscreen is used to manage touch-gesture responses of the 107-computer signal governance of electricity from source 102 via its input to the cpu pursuant to user touch engagement. The said computer response signaling scenarios regard piston compression operation and outflow controlling of dispensed compressed vapor from 120 the dispense valve. The touchscreen functions allow engagement/disengagement management of computer distribution to the mechanisms functioning piston/motor compression, as well as control of the release function of the 120 valve.

104 the flexible hookah style discharge hose is designed to simulate traditional hookah/shisha. It is junctioned to the release or outlet side of the valve 120 to receive outputted compressed atomized vapor and through the length of its structure, ultimately transfer outputted compressed dispensed vapor from 120 valve to the final downstream location which is the likewise hookah-style 105 inhalation nipple/mouthpiece, which the user places his or her mouth upon and wherein the vapor is outed from this point of the machine for direct inhalation.

TECHNICAL PROBLEM AND SOLUTION

The problem that exists today is that there is a market need, currently, that takes advantage of the social aspects of smoking in the context of electronic cigarettes, and younger generation, and although many vape in social settings, the designs of contemporary vapes a certainly geared toward solitary use. The goal is to address this market need by applying to the younger generation. Hookah is the most social of all smoking events, however, no other form of smoking is as socially involved. Electronic cigarettes, while often found at social events, have a base of consumers who do vape socially, with the lack of a new product (for that consumer market) that fully taps into the social aspects of the smoking market and sub culture. The problem is solved because a solution is created for the need to tap into the social aspects of smoking, as it applies to the electronic cigarette industry. The invention has manifested itself as an electronic cigarette machine. The invention solves a marketing need by creating a highly marketable application of the new e-cigarette market, and the hookah market, combining them so that an enjoyable article of manufacture is created. it is marketable towards the social smoking sub-crowd, as seen with contemporary hookah, and often overlooked in more solitary vape-pen designs. The marketability of the invention is complimented further by the hookah style design, and modern application of the digitizer touchscreen. As stated, the marketing solution of the invention by the touchscreen panel which has high-tech market appeal.

ADVANTAGES

The solution is a unit not only capable of providing enough smoke for a social hookah experience, but has the potential to produce large quantities of smoke production never achieved before in the electronic cigarette world.

DRAWINGS

Figure 1:
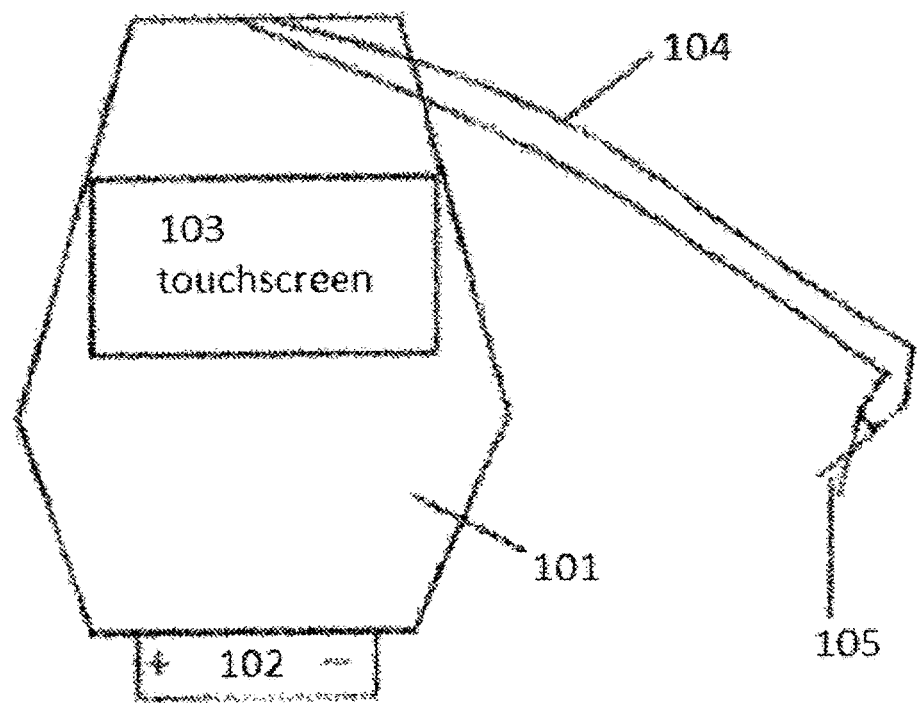
FIG. 1 is a front view of the outside of the atomization/compression hookah machine.
Figure 2:
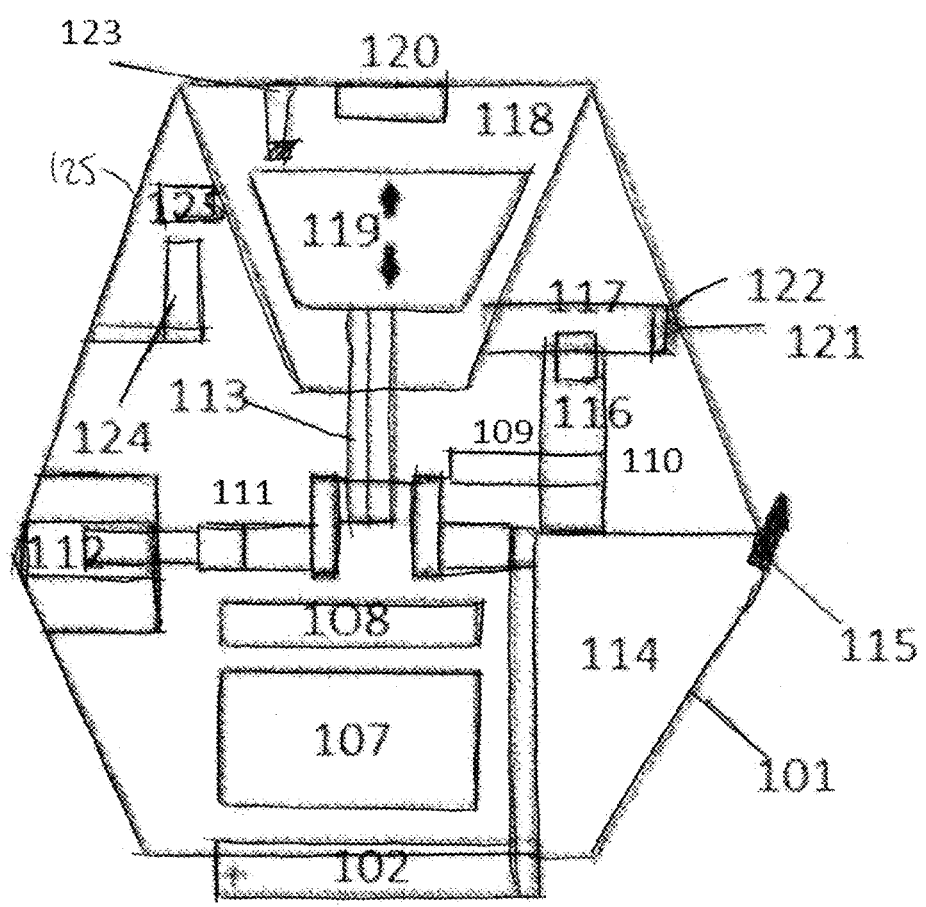
FIG. 2 is an internal mechanical parts/components diagram.

EMBODIMENT FIGURES 101 housing/shell;
102 battery;
103 touchscreen operation panel interface;
104 hookah-style flexible hose;
105 hookah-style inhalation mouthpiece;
107 computer chip or circuit;
108 atomizer circuit path coil;
109 atomizer path electric connection terminals;
110 atomizer;
111 compression crankshaft;
112 compression electric motor;
113 piston connecting rod;
114 refillable liquid chamber/reservoir/tank;
115 fill junction for reservoir/tank;
117 atomizer/compression chamber junction;
118 compression piston chamber;
119 compression piston;
120 dispense valve;
121 fan motor;
122 fan;
123 electromagnetic piston assist rod;
124 electromagnetic rod coil;
125 crankshaft position sensor.

What is claimed is:

1. A vaporizer comprising a housing; and a heating element wherein inhalation matter generated by the heating element is mechanically compressed, via compaction in an enclosed capacity by a reciprocating type compression system located within the housing, after it has been generated, prior to or consistent with its dispense from the vaporizer for user inhalation.

2. The vaporizer of claim 1 wherein the heating element is an atomizer; wherein the inhalation matter is vapor.

3. The vaporizer of claim 2 further comprising a refillable storage capacity for liquid that is convert-able into the inhalation mater by the atomizer.

4. The vaporizer of claim 1 further comprising a computer control system.

5. The vaporizer of claim 1 further comprising a touchscreen.

6. The vaporizer of claim 1 further comprising an inhalation mouthpiece.

7. The vaporizer of claim 1 further comprising a valve that regulates the output of the inhalation matter from the vaporizer.

8. The vaporizer of claim 1, wherein the vaporizer further comprises a fan.

9. The vaporizer of claim 6 further comprising a hose junctioned on one end of its length to the vaporizer's output of inhalation matter, and junctioned on the other, most downstream end of its length, respective of the vaporizer's processing and dispense of inhalation matter, to the inhalation mouthpiece, wherein inhalation matter is ultimately, and finally outputted through the inhalation mouthpiece located at the end of the hose, for user inhalation.

10. The vaporizer of claim 4 wherein a touchscreen is used to modify processing of the computer control system, thereby influencing the compression and/or dispensing functions, respective of the inhalation matter, that are performed by the vaporizer.

* * * * *